United States Patent [19]

Hosgood et al.

[11] Patent Number: 4,858,469

[45] Date of Patent: Aug. 22, 1989

[54] METHOD AND APPARATUS FOR TESTING TIMBERS FOR DISCONFORMITY OR DECAY

[75] Inventors: Henry Hosgood; Leslie Banks, both of Dorset; William Beauford, Somerset, all of England

[73] Assignee: Bio-Kil Chemicals Limited, London, England

[21] Appl. No.: 97,219

[22] Filed: Sep. 15, 1987

[30] Foreign Application Priority Data

Sep. 20, 1986 [GB] United Kingdom ................. 8622731

[51] Int. Cl.⁴ ..................... G01H 13/00; G01N 29/00; G01N 29/04
[52] U.S. Cl. .......................................... 73/579; 73/600
[58] Field of Search .................... 73/579, 600

[56] References Cited

U.S. PATENT DOCUMENTS

| | | | |
|---|---|---|---|
| 3,531,983 | 10/1967 | Heath | 73/579 |
| 3,877,294 | 4/1975 | Shaw | 73/579 |
| 4,059,988 | 11/1977 | Shaw | 73/579 |
| 4,350,044 | 9/1982 | Richardson et al. | 73/600 |
| 4,399,701 | 8/1983 | Dunlop | 73/579 |
| 4,502,329 | 3/1985 | Fukunaga et al. | 73/579 |
| 4,635,483 | 1/1987 | Mishiro | 73/579 |
| 4,702,111 | 10/1987 | Holland | 73/579 |

*Primary Examiner*—Stewart J. Levy
*Assistant Examiner*—Robert P. Bell
*Attorney, Agent, or Firm*—Kane, Dalsimer, Sullivan, Kurucz, Levy, Eisele and Richard

[57] ABSTRACT

A method for testing timbers, such as railway sleepers, for disconformities or decay by inducing vibrations in the timber, for example with an impactor monitored by an accelerometer mounted on it and connected to a microprocessor and a display unit to give an indication of constant impact, detecting said vibrations by one or more transducers, amplifying and digitizing the transducer output and microprocessor-processing the digitized output to give an indication of disconformity or decay. One embodiment utilizes the comparison of the first half-cycle surface vibrations and shear vibrations. Another embodiment compares frequency domain information with a memory stored standard. The apparatus, comprising transducers, impactor, microprocessor and indicator is readily portable.

7 Claims, 4 Drawing Sheets

METHOD AND APPARATUS FOR TESTING TIMBERS FOR DISCONFORMITY OR DECAY

BACKGROUND OF THE INVENTION

1. Field of the Invention

This invention relates to a method for testing timbers for decay and to equipment for use in such a process.

2. Brief Description of the Prior Art

Timbers for long duration external use such as, for example, utility poles or railway sleepers often have a predictable life span. However, despite a usual initial treatment with a coal tar creosote or a like product the presence of cracks in individual timbers may eventually allow the ingress into the interior of a timber of decay inducing organisms, such as fungi. Since it is clearly uneconomic and disruptive to replace or treat timbers without prior knowledge of the extent of decay, if any, of each timber it is necessary to identify decayed timbers "in situ" and by a non destructive means of testing, so that they may be replaced or treated individually with minimal disturbance.

The present invention relates generally to a method for testing timbers by causing vibrations in the timber and detecting the vibrations so as to identify characteristics associated with the passage of the vibrations through decayed timber. Methods of the above type have been proposed previously.

According to one such method, described in British Pat. No. 1153238, a sonic transducer is placed on the surface of the timber at a point opposite to the point at which the vibration is generated, a filter circuit connected to the transducer divides the signals so detected into preselected high and low frequency segments and the energy in the two segments is compared on the basis that in decayed timber the majority of the energy will be in the low frequency segment.

According to a further such method, described in British Pat. No. 1175719, pulses of accoustical energy transmitted through a pole are compared with those transmitted through a known defect and rot-free pole of the same timber, a longer pulse duration and/or a lower frequency being taken to be indicative of the presence of decay.

SUMMARY OF THE INVENTION

The present invention utilises a new concept in timber testing and provides a method for testing timber for disconformities or decay comprising inducing vibrations in the timber, detecting the vibrations by means of one or more transducers in contact with the timber or adjacent to its surface and passing the transducer output to processing means adapted to detect patterns in said output characteristic of decay and to trigger an indicating device on so doing, the method being characterised by the conversion of the transducer output into digital form and the processing of said digitised output by microprocessor arranged to trigger said indicating means.

DETAILED DESCRIPTION OF THE PREFERRED EMBODIMENTS OF THE INVENTION

Figure 1:
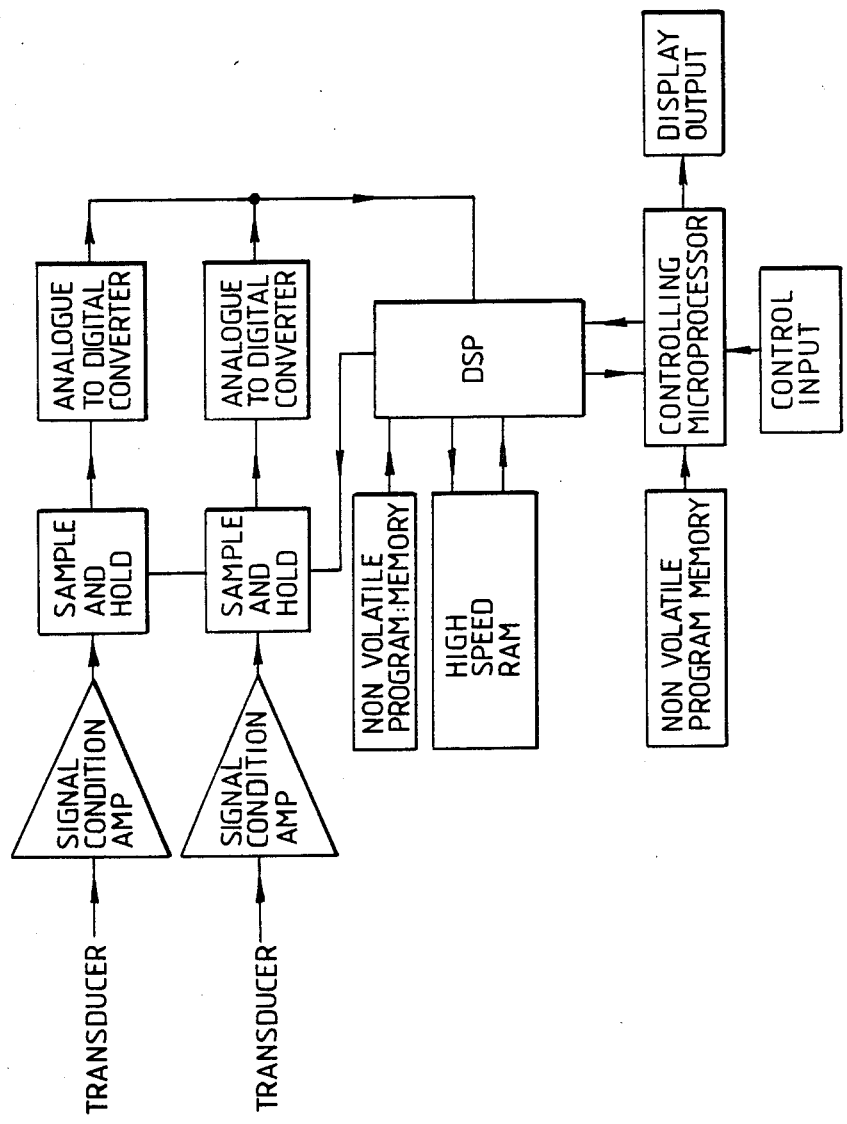
FIG. 1 is a schematic representation of embodiment hardware and its interconnection to form a signal analysis system.

The power and versality of the modern microprocessor enable a variety of new parameters indicative of disconformities or decay in the timber to be established.

The means for inducing vibrations or waves in the timber may be an impactor which is, desirably, capable of applying to the timber a given force which is sufficiently great to set the timber into motion. Constant impact hammers are known and may, for example, be pneumatically or gravity deriven or may be driven by a solenoid or may even ba manually applied. Preferably the impactor has a working surface of a constant shore hardness which is suitable to cause excitation of the timber to the desired frequency and without causing undue surface damage. It is highly desirable that the impact be constant as between successive impacts at one or more sites on the timber or even between different timbers. Preferably, therefore, a transducer capable of measuring the acceleration and/or force of the impact is mounted on the impactor said transducer being connected to microprocessor means having a memory-stored standard and arranged to be capable of comparing said transducer output with said standard and to be capable of indicating deviance or non-deviance or the extent of deviance from said standard thereby providing a means for monitoring and/or controlling the impact to conform to said standard. The indicating means may be digital readout of deviance, lights colour coded to indicate deviance or non-deviance or any other suitable means known to the art. The output from the transducer may be processed in the time domain or in the frequency domain but preferably in the latter.

The means for detecting vibrations in timber may be of any suitable type. Detection of surface vibrations can be achieved using a microphone, pressure transducer or accelerometer. The internally transmitted or shear vibrations can be measured using an accelerometer or any other suitable transducer coupled or in contact with the timber. Coupling can be achieved using a pin, capable of being driven into the timber for example, to a depth of at least 10 mm, preferably from 20 to 50 mm or via seismic block with an attached transducer. The microphone may preferably be held at a vertical distance of 1 to 5 mm from the surface of the timber. The pressure transducer may be held in contact with the surface of the timber as may the siesmic block. Other suitable transducers will be known to these in the art. Combination of different types of transducers may be used as will be described hereafter.

According to a first preferred aspect thereof the present invention provides a method for testing timbers comprising the separate detection and comparison of surface vibrations and internally transmitted vibrations from the same source of energy e.g. the same impact. Such a concept is of itself new in the art. The present invention therefore provides a method for testing timbers comprising causing vibrations in the timber by impact, separately detecting surface vibrations and shear vibrations caused by said impact by suitable transducer means converting the transducer outputs into digital form and processing said digitised outputs on a microprocessor to detect disconformities therebetween. Very suitably the transducer for detecting surface vibrations, for example, a microphone, is placed close to, for example from 5 to 20 mm from, the point of measurement of the internally transmitted vibrations. Preferably both transducers are placed adjacent to an area of suspected decay or so that the suspected decay is between the point of impact and the transducers.

It has been found that, while there is a similarity between the frequency and/or amplitude of surface waves and internally transmitted vibrations in the first half cycle in sound timber there is a particularly distinct disconformity between them in decayed timber. In order to put this embodiment of the invention into effect it is necessary to ensure that the transient signal capture device is triggered at the instant of signal commencement in order to capture the desired first half cycles.

According to further aspects of this invention other characteristic patterns of amplitude and frequency within the respective overall signal envelopes which have also been found to indicate the extent of decay and also the presence of voids are monitored. No such patterns occur where the timber is sound.

According to a second and separate aspect of the present invention which is not limited to the utilisation of a first half cycle of vibration there is provided a method for testing timbers comprising comparing the frequency signature of a sample of vibration with that of a sample of sound timber. According to this aspect of the invention either surface vibrations or shear vibrations may be utilised as the source of the frequency signature and the position of one or more transducers for the detection of such vibrations is a matter of operator choice, said position being either distant from the source of the impact or close to it, or even being measured via a further transducer mounted in the impact head. When processed according to the present invention by converting the time domain data collected via a suitable transducer to frequency domain data it is found that, whether the transducer is capable of detecting surface or shear vibrations, the resulting frequency domain data is sufficiently characteristic to enable it to be compared with a memory stored standard. The data from the transducer is filtered and windowed prior to conversion this being suitably achieved by using a Discrete Fourier Transform within the digital signal processor employed according to this invention. This embodiment of the present invention is very simple in practical application and has shown itself to be highly reliable in detecting decay. The memory-stored standard frequency domain data is preferably represented by a data base of such data obtained, using the same standard impact previously described, from a range of timbers of the same variety of differing states of decay. The microprocessor may be arranged to accept only identity with the sound timber data or deviation therefrom by only a preset degree corresponding with a certain possibly only slight, degree of decay in the timber. This method is capable of monitoring the degree of decay with considerable accuracy.

One method and apparatus for putting the aforementioned further aspect of the invention into effect is as follows, reference being made to FIG. 1 which is schematic representation of the hardware and its interconnection to form a signal analysis system.

A hammer, computer-monitored by means of a transducer thereon for constant impact so as to allow the operator to control the impact to a substantially constant level, is used together with one or more transducers, suitably a pinmounted accelerator.

The analysis equipment is based on a digital signal processor (DSP) fed by a non-volatile program memory and interacting with a high speed random access memory (RAM). The digital signal processor is connected to each vibration-sensing transducer via a fast high speed analogue to digital converter with tristate digital buffer, a sample and hold device driven from the internal DSP clock and a signal conditioning amplifier (AMP). Also interconnected with the digital signal processor is a controlling microprocessor under the control of program stored in a non-volatile program memory, the controlling microprocessor being also connected to a suitable display unit.

In operation signals are fed to the signal-conditioning amplifiers which are matched to their appropriate transducers. The output from the amplifiers is transferred via the sample and hold devices to the digital convertors. The digital bus connects to the DSP and output data lines select the incoming data as required. The non-volatile memory attached to the DSP stores the Discrete Fourier Transform alogrithim and along with appropriate control lines from the controlling microprocessor performs the transformation of the data from the data time base to frequency domain. Window capturing is achieved by pretriggering. The non-volatile memory also stores the controlling program and the reference data base attached to the controlling microprocessor. All software is preferably written in machine code for speed and efficiency although it may be implemented at a higher level. Sequence and mode of operation is fed from switches to the controlling microprocessor allowing a variety of assessments.

While the above description is in terms of function suitable equipment for use in the practice of either aspect of the present invention may readily be selected and assembled by those skilled in the art. For example, suitable signal conditioning amplifiers, sample and hold devices and analogue to digital converters are currently supplied by Analogue Devices Limited. A suitable digital signal processor is the Texas Instruments Model TMF 320-C25. A sutable controlling microprocessor is the Monolithic Memories PAL Device 20 RS8. The non-volatile and RAM memories may readily be selected with capacities corresponding to the requirements. Other equipment and accessories may likewise be obtained from major electronics suppliers.

The technique described herein can be applied to a range of timber commodities, such as transmission (utility) poles, joinery and, particularly, railway sleepers. The detection of decay by the "in situ" technique can be applied to softwood and hardwood railway sleepers. Typically the softwood sleepers used in the United Kingdom are 240 cm×25 cm×15 cm utilising either European Redwood (*Pinus sylvestris*) or Douglas Fir (*Pseudotsuga menziesii*). The apparatus comprising transducers, impactor, microprocessor and indicating means is readily portable.

Both the first and second above described preferred aspects of the present invention have been found to give a reliable indication of internal decay in timbers. A trial of the above described first preferred aspect of the invention is now described with reference to FIGS. 2 and 3 attached hereto.

Figure 2:
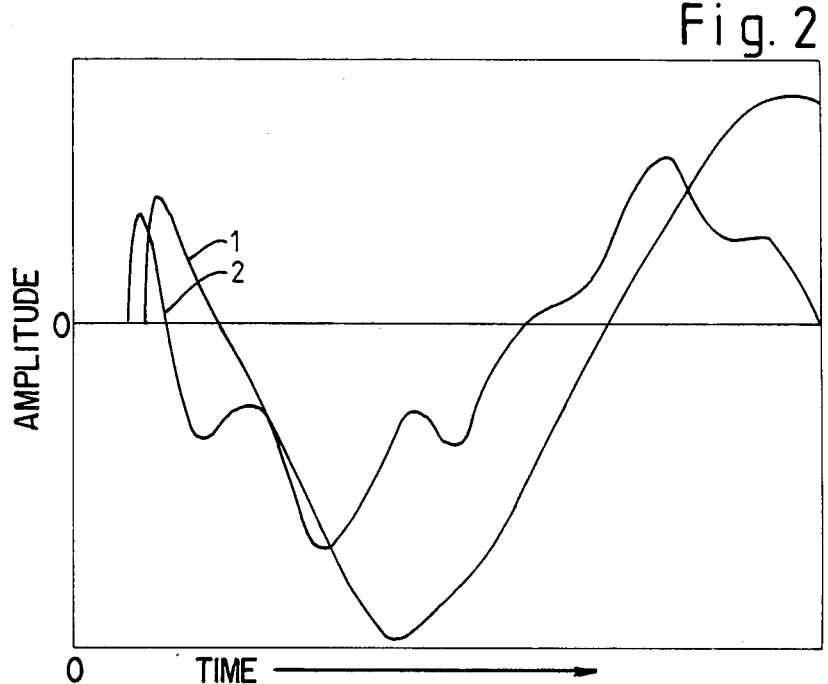
FIG. 2 shows the amplitude of frequency waves detected by use of the embodiment system of FIG. 1, on a structurally sound railroad sleeper.
Figure 3:
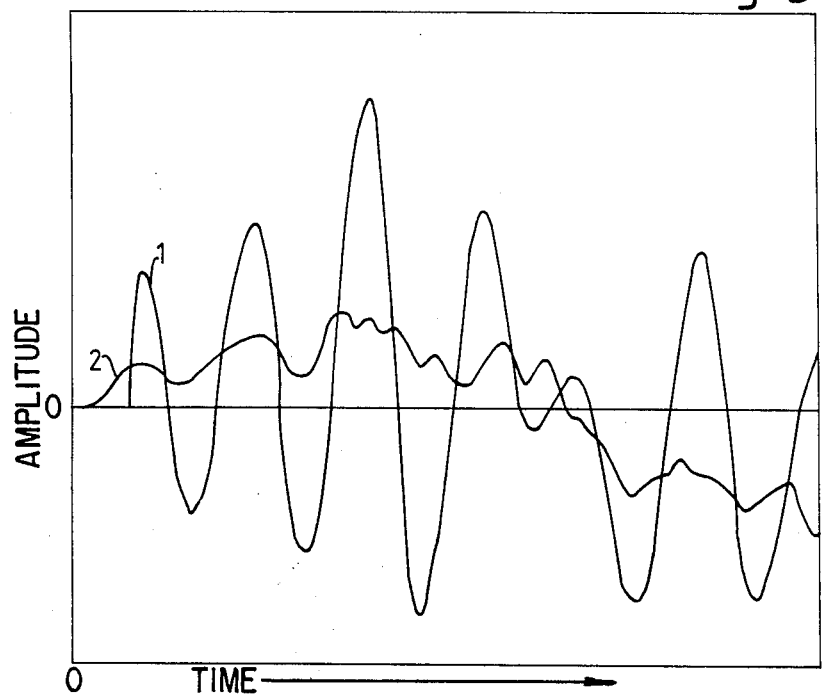
FIG. 3 is a tracing as in FIG. 2, but obtained on an internally decayed sleeper.

In this trial railway sleepers of the same timber were tested. The results are depicted in FIGS. 2 and 3 attached hereto of which FIG. 2 relates to a sound sleeper and FIG. 3 relates to an internally decayed sleeper. In each Figure trace 1 is derived from the internally transmitted vibrations and trace 2 is derived from the surface waves. FIGS. 2 and 3 show the amplitude of frequency waves detected by the transducer capable of detecting shear waves (trace 1) and by that capable of detecting surface waves (trace 2). The distinctions between these two traces and between sound and decayed timber, both with regard to the first half cycles and to the overall signal configuration, are clearly visible.

A trial of the above described second preferred aspect of the invention is now described with references to FIGS. 4 to 9 attached hereto utilising the conversion of time domain data into the frequency domain. Each of the Figures depicts a plot of frequency measured in KHz versus intensity measured in dB for a windowed sample of digitised output from a transducer.

Figure 4:
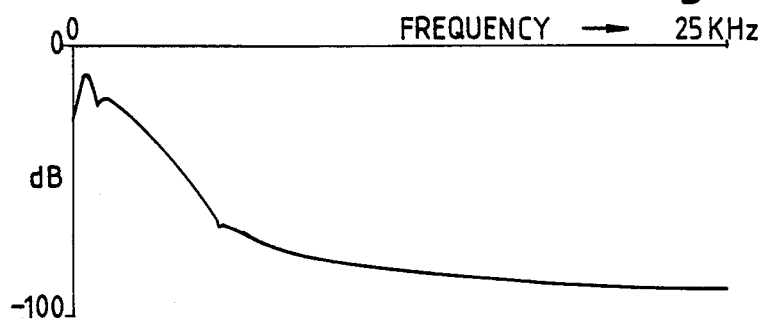
FIGS. 4, 5 and 6 show, respectively, impact waves, shear waves and surface waves obtained by use of the system of FIG. 1 carried out on a sound, undecayed, timber sleeper.
Figure 5:
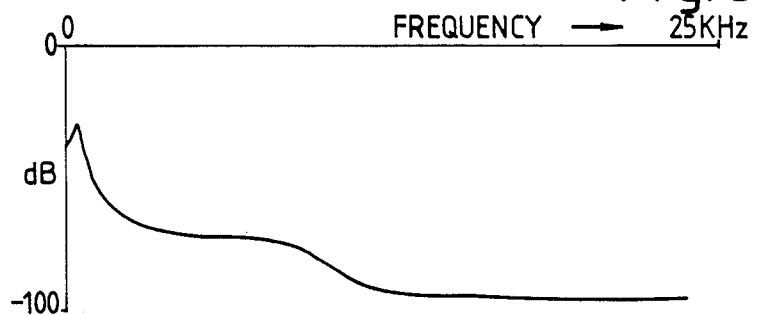
Figure 6:
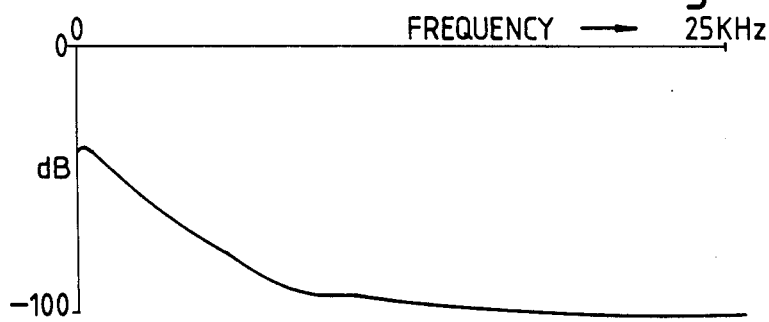
Figure 7:
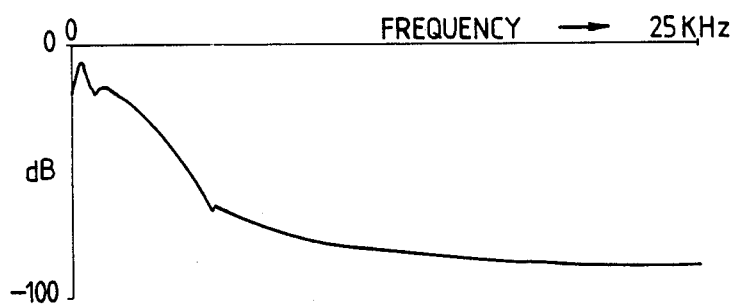
FIGS. 7, 8 and 9 show, respectively, impact waves, shear waves and surface waves obtained by use of the system of FIG. 1 carried out in an internally decayed sleeper.
Figure 8:
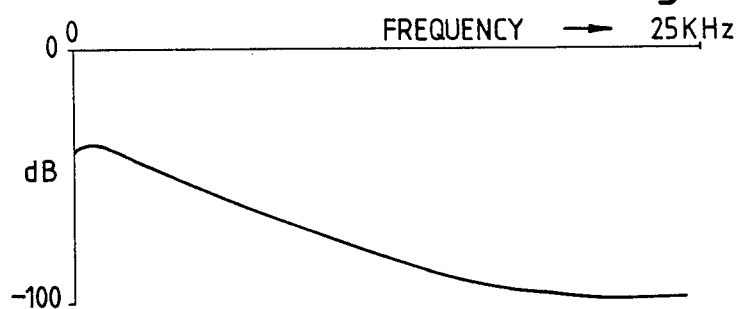
Figure 9:
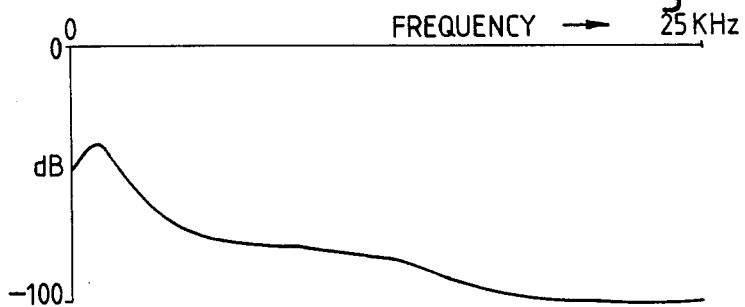

FIGS. 4, 5 and 6 relate respectively to impact waves (transducer mounted on impact hammer), shear waves (transducer being an accelerometer mounted on a pin embedded in the timber) and surface waves (transducer being a microphone held 1 mm from the timber surface) obtained from a sound, un-decayed, timber sleeper. FIGS. 7, 8 and 9 relate respectively to the same waves from an internally decayed sleeper.

The substantial identity of FIGS. 4 and 7 confirm that a constant impact is in use in both cases. The distinction between curves 5 and 8 and also between curves 6 and 9 is visible and is readily distinguished by the microprocessor.

What is claimed is:

1. A method for testing timber for disconformity or decay, which comprises:

inducing vibrations in the timber;

detecting by separate transducers and as to amplitude in the time domain at least the first half cycle of the surface vibrations and of the shear vibrations in the timer;

amplifying the transducer outputs;

processing the amplified outputs by a microprocessor connected to an indicator, said microprocessor being adapted to compare at least the portions of the amplified outputs corresponding to the said first half cycle and the indicator being adapted to indicate when a disconformity is detected between the compared outputs.

2. A method as claimed in claim 1 wherein the vibrations in the timber are induced by an impactor monitored by a microprocessor acting on output from a transducer mounted on the impactor to enable a substantially constant impact to be applied.

3. A method as claimed in claim 1 wherein the transducer capable of detecting surface vibrations is selected from the group comprising microphones, pressure transducers and accelerometers.

4. A method as claimed in claim 1 wherein the shear vibrations are detected by a transducer coupled to a pin driven into the timber or coupled to a seismic block in contact with the timber.

5. A method as claimed in claim 1 wherein the amplified signals are converted to digital form before processing by the microprocessor.

6. Apparatus for testing timber for disconformity or decay comprising a means for inducing vibrations in the timber, signal conditioning amplifiers each connected to a respective one of a transducer capable of detecting shear vibrations and a transducer capable of detecting surface vibrations each amplifier being connected via a sample and hold device and to a microprocessor and an indicator connected thereto, the apparatus being capable of separately detecting at least the first half-cycle of the shear vibrations and the surface vibrations induced in the timber as to their amplitude in the time domain, of comparing the signals derived form the said first half-cycle and indicating the presence of disconformity between the compared signals.

7. Apparatus as claimed in claim 6 wherein the sample and hold device is connected to the microprocessor via an analogue to digital converter.

* * * * *